US006200775B1

United States Patent
Ellis et al.

(10) Patent No.: US 6,200,775 B1
(45) Date of Patent: Mar. 13, 2001

(54) CDNA CLONE HMTMF81 THAT ENCODES A NOVEL HUMAN 7-TRANSMEMBRANE RECEPTOR

(75) Inventors: Catherine E. Ellis, Glassboro, NJ (US); Wendy Halsey, Kennett Square, PA (US); Ganesh M. Sathe, King of Prussia, PA (US); Robert S. Ames, Havertown, PA (US); James J. Foley, Radnor, PA (US); Henry M. Sarau, Harleysville, PA (US); Jon Chambers, Haslingfield (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/044,404

(22) Filed: Mar. 19, 1998

Related U.S. Application Data

(63) Continuation-in-part of application No. 08/844,795, filed on Apr. 22, 1997, now abandoned.

(51) Int. Cl.[7] ............................. C12N 15/12; C12N 5/10; C07K 14/705
(52) U.S. Cl. .................. 435/69.1; 435/252.3; 435/320.1; 530/350; 536/23.5
(58) Field of Search ............................ 435/69.1, 252.3, 435/320.1; 530/350; 536/23.5

(56) References Cited

U.S. PATENT DOCUMENTS

| | | |
|---|---|---|
| 5,508,384 | 4/1996 | Murphy et al. . |
| 5,556,780 | 9/1996 | Dzau et al. . |

FOREIGN PATENT DOCUMENTS

| | | |
|---|---|---|
| WO96/05302 | 2/1996 | (WO) . |
| WO96/41169 | 12/1996 | (WO) . |

OTHER PUBLICATIONS

Oliviveira et al., "A common motif in G–protein–coupled seven transmembrane helix receptors," J. of Computer–Aided Molecular Design, vol. 7, No. 6, pp. 649–658 (1993).

Hendersen, "The Role of Leukotrienes in Inflammation," Annals of Internal Medicine, vol. 121, No. 9, pp. 684–697 (1994).

Capra et al., "Identification and Characterization of two cysteinyl–leukotriene high affinity binding sites with receptor characteristics in human lung parenchyma," Molecular Pharmacology, vol. 53, No. 4, pp. 750–758 (1998).

Kaplan et al. Identification of a G Protein Coupled Receptor Induced in Activated T Cells. J. of Immunol. vol. 151:628–636, Jul. 15, 9.*

Human Genome Sciences Corporation EST #1558415, Apr. 22, 1997.

GenBank Accession #X56736 Apr. 4, 1991.
GenBank Accession #P49651, Feb. 1, 1996.
GenBank Accession #I26127, Sep. 20, 1996.
GenBank Accession #S73388, Jan. 18, 1995.

Tokuyama et al., "Cloning of Rat and Mouse $P_{2Y}$ Purinoceptors", Biochem. & Biophysical Research Communications, vol. 211, No. 1, pp. 211–218, Jun. 1995.

Honda et al., Nature, "Cloning by functional expression of platelet–activating factor from receptor guinea–pig lung", vol. 349, pp. 342–346, Jan. 1991.

Nishimatsu et al., "Isolation and characterization of two alternatively spliced complementary DNAs encoding a *Xenopus laevis* angiotensin II receptor", Biochimica et Biophysica Acta, vol. 1218, pp. 401–407, (1994).

George et al., "Current Methods in Sequence Comparison and Analysis", Macromolecular Sequencing and Synthesis, Alan R. Liss, Inc. Chptr. 12, pp. 127–149 (1988).

\* cited by examiner

*Primary Examiner*—John Ulm
(74) *Attorney, Agent, or Firm*—Elizabeth J. Hecht; Ratner & Prestia; William T. King

(57) ABSTRACT

HMTMF81 polypeptides and methods for producing such polypeptides by recombinant techniques are disclosed. Also disclosed are methods for utilizing HMTMF81 polypeptides and polynucleotides in the design of protocols for the treatment of infections such as bacterial, fungal, protozoan and viral infections, particularly infections caused by HIV-1 or HIV-2; anorexia; bulimia; asthma; Parkinson's disease; acute heart failure; hypotension; hypertension; urinary retention; osteoporosis; angina pectoris, myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others and diagnostic assays for such conditions.

11 Claims, No Drawings

CDNA CLONE HMTMF81 THAT ENCODES A NOVEL HUMAN 7-TRANSMEMBRANE RECEPTOR

CROSS REFERENCE TO RELATED APPLICATIONS

This is continuation-in-part application of U.S. Ser. No. 08/844,795 filed Apr. 22, 1997, now abandoned, which is herein incorporated by reference in its entirety.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to G-protein coupled receptor, hereinafter referred to as HMTMF81. The invention also relates to inhibiting or activating the action of such polynucleotides and polypeptides. The invention further relates to inhibiting or activating the action of LTD4 and LTC4.

BACKGROUND OF THE INVENTION

It is well established that many medically significant biological processes are mediated by proteins participating in signal transduction pathways that involve G-proteins and/or second messengers, e.g., cAMP (Lefkowitz, Nature, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K., et al., Proc. Natl Acad. Sci., USA, 1987, 84:46–50; Kobilka, B. K., et al., Science, 1987, 238:650–656; Bunzow, J. R., et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect of hormone binding is activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said socket being surrounded by hydrophobic residues of the G-protein coupled receptors. The hydrophilic side of each G-protein coupled receptor transmembrane helix is postulated to face inward and form polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc. Rev., 1989, 10:317–331) Different G-protein a-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 transmembrane (7 TM) receptors have been successfully introduced onto the market.

This indicates that these receptors have an established, proven history as therapeutic targets. Clearly there is a need for identification and characterization of further receptors which can play a role in preventing, ameliorating or correcting dysfunctions or diseases, including, but not limited to, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

SUMMARY OF THE INVENTION

In one aspect, the invention relates to HMTMF81 polypeptides and recombinant materials and methods for their production. Another aspect of the invention relates to methods for using such HMTMF81 polypeptides and polynucleotides. Such uses include the treatment of infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. In still another aspect, the invention relates to methods to identify agonists and antagonists using the materials provided by the invention, and treating conditions associated with HMTMF81 imbalance with the identified compounds. Yet another aspect of the invention relates to diagnostic assays for detecting diseases associated with inappropriate HMTMF81 activity or levels.

DESCRIPTION OF THE INVENTION

Definitions

The following definitions are provided to facilitate understanding of certain terms used frequently herein.

"HMTMF81" refers, among others, to a polypeptide comprising the amino acid sequence set forth in SEQ ID NO:2, or an allelic variant thereof.

"Receptor Activity" or "Biological Activity of the Receptor" refers to the metabolic or physiologic function of said HMTMF81 including similar activities or improved activities or these activities with decreased undesirable side-effects. Also included are antigenic and immunogenic activities of said HMTMF81.

"HMTMF81 gene" refers to a polynucleotide comprising the nucleotide sequence set forth in SEQ ID NO: 1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New. York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Posttranslational Modifications and Aging", Ann NY Acad Sci (1992) 663:48–62. "Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM J. *Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Preferred parameters for polypeptide sequence comparison include the following:
1) Algorithm: Needleman and Wunsch, J. Mol Biol. 48: 443–453 (1970)
Comparison matrix: BLOSSUM62 from Hentikoff and Hentikoff, Proc. Natl. Acad. Sci. USA. 89:10915–10919 (1992)
Gap Penalty: 12
Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:
1) Algorithm: Needleman and Wunsch, J. Mol Biol. 48: 443–453 (1970)
Comparison matrix: matches=+10, mismatch=0
Gap Penalty: 50
Gap Length Penalty: 3

Available as: The "gap" program from Genetics Computer Group, Madison Wis. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO: 1 by the numerical percent of the respective percent identity (divided by 100) and subtracting that product from said total number of nucleotides in SEQ ID NO:1, or:

$$n_n \le x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%,etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \le x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"LTD4" or leukotriene $D_4$ ($LTD_4$) has the chemical structure (5S, 6R)-6-S-cysteinylglycine-5-hydroxy-(7Z, 9Z, 11E, 14E)-eicosatetraenoic acid, and is described, for example, by Barnes NC, de Jong B, Miyamoto T, in *Chest* 1997 Feb;111(2 Suppl):52S-60S, *Worldwide clinical experience with the first marketed leukotriene receptor antagonist.*

"LTC4" or leukotriene $C_4$ ($LTC_4$) has the chemical structure ([5S,6R]-5-hydroxy-6-(5-glutathionyl)-(7E,9E,11Z, 14Z]-eicosatetraeonic acid. LTC4 is described, for example, in McIntyre, T. M., Zimmerman, G. A. and Prescott, S. M. *Leukotrienes C4 and D4 stimulate human endothelial cells to synthesize platelet-activating factor and bind neutrophils.* Proc. Natl. Acad Sci (USA), 83, 2204–2208, 1986; Tamura, N., Agrawal, D. K. and Townley, R. G. *A specific assay for leukotriene C4 and the measurement of calcium ionophore-induced leukotriene C4 production from human leukocytes.* J Pharm. Methods 18, 327–333, 1987; Owen, W. F., Soberman, R. J., Yoshimoto, T., Sheffer, A. L., Lewis, R. A. and Austen, K. F. *Synthesis and release of leukotriene C4 by human eosinophils.* J Immunology 138, 532–538, 1987.

Polypeptides of the Invention

In one aspect, the present invention relates to HMTMF81 polypeptides. The HMTMF81 polypeptides include the polypeptide of SEQ ID NO:2; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within HMTMF81 polypeptides are polypeptides having the amino acid sequence which have at least 80% identity to the polypeptide having the amino acid sequence of SEQ ID NO: 2 over its entire length, and still more preferably at least 90% identity, and even still more preferably at least 95% identity to SEQ ID NO: 2. Furthermore, those with at least 97–99% are highly preferred. Preferably HMTMF81 polypeptides exhibit at least one biological activity of the receptor.

The HMTMF81 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the HMTMF81 polypeptides are also included in the invention. A fragment is a polypeptide having an amino acid sequence that entirely is the same as part, but not all, of the amino acid sequence of the aforementioned HMTMF81 polypeptides. As with HMTMF81 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of HMTMF81 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HMTMF81 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate receptor activity, including those with a similar activity or an improved activity, or with a decreased undesirable activity. Also included are those that are antigenic or immunogenic in an animal, especially in a human.

Preferably, all of these polypeptide fragments retain the biological activity of the receptor, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The HMTMF81 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to HMTMF81 polynucleotides. HMTMF81 polynucleotides include isolated polynucleotides which encode the HMTMF81 polypeptides and fragments, and polynucleotides closely related thereto. More specifically, HMTMF81 polynucleotide of the invention include a polynucleotide comprising the nucleotide sequence set forth in SEQ ID NO: 1 encoding a HMTMF81 polypeptide of SEQ ID NO: 2, and polynucleotide having the particular sequence of SEQ ID NO: 1. HMTMF81 polynucleotides further include a polynucleotide comprising a nucleotide sequence that has at least 80% identity to a nucleotide sequence encoding the HMTMF81 polypeptide of SEQ ID NO:2 over its entire length, and a polynucleotide that is at least 80% identical to that having SEQ ID NO: 1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under HMTMF81 polynucleotides are a nucleotide sequence which has sufficient identity to a nucleotide sequence contained in SEQ ID NO: 1 to hybridize under conditions useable for amplification or for use as a probe or marker. The invention also provides polynucleotides which are complementary to such HMTMF81 polynucleotides.

HMTMF81 of the invention is structurally related to other proteins of the G-protein coupled receptor, as shown by the results of sequencing the cDNA encoding human HMTMF81. The cDNA sequence contains an open reading frame encoding a polypeptide of 337 amino acids. Amino acid sequence of Table 1 (SEQ ID NO:2) has about 31.4% identity (using FASTA) in 318 amino acid residues with rat P2Y purinoceptor (Accession No. P49651, Tokuyama, Y et al, Biochem. Biophys. Res. Commun. 211 (1), 211–218, 1995). Furthermore, HMTMF81 (SEQ ID No.2) is 32.4% identical to a protein sequence over 293 amino acid U.S. Pat. No. 5,508,384). Furthermore, HMTMF81 (SEQ ID No. 2) is 32.2% identical to Cavpo platelet activating factor receptor over 298 amino acid residues (Accession No. P21556, Honda, Z. I. et al, Nature, 349 (6307), 342–346, 1991). Nucleotide sequence of Table 1 (SEQ ID NO: 1) has about 53.26% identity (using BLAST) in 368 nucleotide residues with Angiotensin II receptor (Accession No. S73388, Nishimatsu, S et al, Biochem. Biophys. Acta. 1218 (3), 401–407, 1994). Furthermore, HMTMF81 (SEQ ID No.1) is 55% identical to a polynucleotide sequence over 179 base pair residues (U.S. Pat. No. 5,556,780).

The nucleotide sequence encoding HMTMF81 polypeptide of SEQ ID NO:2 may be identical to the polypeptide encoding sequence contained in Table 1 (SEQ ID NO: 1), or it may be a sequence, which as a result of the redundancy (degeneracy) of the genetic code, also encodes the polypeptide of SEQ ID NO: 2.

When the polynucleotides of the invention are used for the recombinant production of HMTMF81 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or TABLE 1[a]

```
   1 CGGCCGCCAGTGTGATGGATATCTGCAGAATTCGGCTTTACGGCTGCGAGAAGACGACAG   60
  61 AAGGGGGAGGAAGAAGAATCTGTATATCTGTATATATTGGCTAGCAAATGTGCCCTGCTC  120
 121 TCTCCCCTCTTAAAAATAGCAGCAACCCATCTTTGCAAAGAAGCTTGCCTATAGAGCAGG  180
 181 CACTCTGTGAATGGACTGTGCTTTTACGACCCTACAGGGTATCAAGATACTGTGCAGCTC  240
 241 GCCAACAAGGATTAATTGCAAGGACTGGTAGATCGAATTTACTGAAGACTTGGAGCTTGC  300
 301 TTCTGAGAACAAACGCAAAAGGACAGTAAACTGTGGACCTTGAAGTTAGCAGCGTGGGCT  360
 361 TCCTCTAATATTACACCGTAAAAGGCATTGATCACCATAAGAAGGAACATTTGTGAAGGT  420
 421 ACTCCAGTGCCAGAAAGAGGCACAAAGCAGACATTCGTAGAGAAACATGGATGAAACAGG  480
 -14                                                M  D  E  T  G    5
 481 AAATCTGACAGTATCTTCTGCCACATGCCATGACACTATTGATGACTTCCGCAATCAAGT  540
   6  N  L  T  V  S  S  A  T  C  H  D  T  I  D  D  F  R  N  Q  V   25
 541 GTATTCCACCTTGTACTCTATGATCTCTGTTGTAGGCTTCTTTGGCAATGGCTTTGTGCT  600
  26  Y  S  T  L  Y  S  M  I  S  V  V  G  F  F  G  N  G  F  V  L   45
 601 CTATGTCCTCATAAAAACCTATCACAAGAAGTCAGCCTTCCAAGTATACATGATTAATTT  660
  46  Y  V  L  I  K  T  Y  H  K  K  S  A  F  Q  V  Y  M  I  N  L   65
 661 AGCAGTAGCAGATCTACTTTGTGTGTGCACACTGCCTCTCCGTGTGGTCTATTATGTCCA  720
  66  A  V  A  D  L  L  C  V  C  T  L  P  L  R  V  V  Y  Y  V  H   85
 721 CAAAGGCATTTGGCTCTTTGGTGACTTCTTGTGCCGCCTCAGCACCTATGCTTTGTATGT  780
  86  K  G  I  W  L  F  G  D  F  L  C  R  L  S  T  Y  A  L  Y  V  105
 781 CAACCTCTATTGTAGCATCTTCTTTATGACAGCCATGAGCTTTTTCCGGTGCATTGCAAT  840
 106  N  L  Y  C  S  I  F  F  M  T  A  M  S  F  F  R  C  I  A  I  125
 841 TGTTTTTCCAGTCCAGAACATTAATTTGGTTACACAGAAAAAAGCCAGGTTTGTGTGTGT  900
 126  V  F  P  V  Q  N  I  N  L  V  T  Q  K  K  A  R  F  V  C  V  145
 901 AGGTATTTGGATTTTTGTGATTTTGACCAGTTCTCCATTTCTAATGGCCAAACCACAAAA  960
 146  G  I  W  I  F  V  I  L  T  S  S  P  F  L  M  A  K  P  Q  K  165
 961 AGATGGGAAAAATAATACCAAGTGCTTTGAGCCCCCACAAGACAATCAAACTAAAAATCA 1020
 166  D  G  K  N  N  T  K  C  F  E  P  P  Q  D  N  Q  T  K  N  H  185
1021 TGTTTTGGTCTTGCATTATGTGTCATTGTTTGTTGGCTTTATCATCCCTTTTGTTATTAT 1080
 186  V  L  V  L  H  Y  V  S  L  F  V  G  F  I  I  P  F  V  I  I  205
1081 AATTGTCTGTTACACAATGATCATTTTGACCTTACTAAAAAAATCAATCAAAAAAAATCT 1140
 206  I  V  C  Y  T  M  I  I  L  T  L  L  K  K  S  M  K  K  N  L  225
1141 GTCAAGTCATAAAAAGGCTATAGGAATGATCATGGTCGTGACCGCTGCCTTTTTAGTCAG 1200
 226  S  S  H  K  K  A  I  G  M  I  M  V  V  T  A  A  F  L  V  S  245
1201 TTTCATGCCATATCATATTCAACGTACCATTCACCTTCATTTTTTACACAATGAAACTAA 1260
 246  F  M  P  Y  H  I  Q  R  T  I  H  L  F  L  H  N  E  T  K  265
1261 ACCGTGTGATTCTGTCCTTAGAATGCACAAGTCCGTGGTCATAACCTTCTCTCTGGCTGC 1320
 266  P  C  D  S  V  L  R  M  Q  K  S  V  V  I  T  L  S  L  A  A  285
1321 ATCCAATTGTTGCTTTGACCCTCTCCTATATTTCTTTTCTGGGGGTAACTTTAGGAAAAG 1380
 286  S  N  C  C  F  D  P  L  L  Y  F  F  S  C  N  F  R  K  R  305
1381 GCTGTCTACATTTAGAAAGCATTGTTTGTCCAGCGTGACTTATGTACCCAGAAAGAAGGC 1440
 306  L  S  T  F  R  K  H  S  L  S  S  V  T  Y  V  P  R  K  K  A  325
1441 CTCTTTGCCAGAAAAAGGAGAAGAAATATGTAAAGTATAGTTTAAACCATTTCCAGTCCA 1500
 326  S  L  P  E  K  G  E  E  I  C  K  V  *                       345
1501 AACCAATGAAAATAGTTTCCCAAATAAGTATTTTGTCAAATCATTTACAAAAAAAAAAAA 1560
1561 AAAAAAAAAAAAAAAAA 1578
```

[a]Nucleotide and deduced amino acid sequence from a human HMTMF81. SEQ ID NOS: 1 and 2, respectively.

One polynucleotide of the present invention encoding HMTMF81 may be obtained using standard cloning and screening techniques from a cDNA library derived from mRNA in cells of human leukocytes and human spleen (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci* USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding HMTMF81 variants comprising the amino acid sequence of HMTMF81 polypeptide of Table 1 (SEQ ID NO:2) in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are identical or sufficiently identical to a nucleotide sequence contained in SEQ ID NO: 1 or a fragment thereof, may be used as hybridization probes for cDNA and genomic DNA, to isolate full-length cDNAs and genomic clones encoding HMTMF81 and to isolate cDNA and genomic clones of other genes that have a high sequence similarity to the HMTMF81 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding HMTMF81 polypeptide comprises the steps of screening an appropriate library under stingent hybridization conditions with a labeled probe having the SEQ ID NO: 1 or a fragment thereof; and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5xSSC (150 mM NaCl, 15 mM trisodium citrate), 50 mM sodium phosphate (pH7.6), 5x Denhardt's solution, 10% dextran sulfate, and 20 microgram/ml denatured, sheared salmon sperm DNA, followed by washing the filters in 0.1x SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli,* Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HMTMF81 polypeptide is to be expressed for use in screening assays, generally, it is preferred that the polypeptide be produced at the surface of the cell. In this event, the cells may be harvested prior to use in the screening assay. If HMTMF81 polypeptide is secreted into the medium, the medium can be recovered in order to recover and purify the polypeptide; if produced intracellularly, the cells must first be lysed before the polypeptide is recovered.

HMTMF81 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of HMTMF81 polynucleotides for use as diagnostic reagents. Detection of a mutated form of HMTMF81 gene associated with a dysfunction will provide a diagnostic tool that can add to or define a diagnosis of a disease or susceptibility to a disease which results from under-expression, over-expression or altered expression of HMTMF81. Individuals carrying mutations in the HMTMF81 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HMTMF81 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc Natl Acad Sci* USA (1985) 85: 4397–4401. In another embodiment, an array of oligonucleotides probes comprising HMTMF81 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome through detection of mutation in the HMTMF81 gene by the methods described.

In addition, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, can be diagnosed by methods comprising determining from a sample derived from a subject an abnormally decreased or increased level of HMTMF81 polypeptide or HMTMF81 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an HMTMF81, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the HMTMF81 polypeptides. The term "immunospecific" means that the antibodies have substantiall greater affinity for the polypeptides of the invention than their affinity for other related polypeptides in the prior art.

Antibodies generated against the HMTMF81 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against HMTMF81 polypeptides may also be employed to treat infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

Vaccines

Another aspect of the invention relates to a method for inducing an immunological response in a mammal which comprises inoculating the mammal with HMTMF81 polypeptide, or a fragment thereof, adequate to produce antibody and/or T cell immune response to protect said animal from infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. Yet another aspect of the invention relates to a method of inducing immunological response in a mammal which comprises, delivering HMTMF81 polypeptide via a vector directing expression of HMTMF81 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a HMTMF81 polypeptide wherein the composition comprises a HMTMF81 polypeptide or HMTMF81 gene. The vaccine formulation may further comprise a suitable carrier. Since HMTMF81 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

This invention encompasses the novel discovery that LTD4 and LTC4, albeit in lower potency, use HMTMF81 polypeptide as their receptor. We discovered this receptor/ligand relationship by conducting experiments that show that LTD4 and LTC4 induce calcium mobilization responses in a HMTMF81 expressing cell line.

Therefore, another aspect of the present invention provides methods of screening for compounds which bind to and activate (agonist) or inhibit activation (antagonist) of human HMTMF81 polypeptides (receptors) and/or their ligand, LTD4 or LTC4, and interactions thereof.

In particular, the preferred method for identifying an agonist or antagonist comprises the steps of:

(a) in the presence of labeled or unlabeled ligand, contacting a cell expressing on the surface thereof HMTMF81 polypeptide (preferably that of SEQ ID NO: 2), said HMTMF81 polypeptide being associated with a second component capable of providing a detectable signal in response to the binding of said ligand, with a compound to be screened under conditions to permit binding to the human HMTMF81 polypeptide; and (b) determining whether the compound binds to and activates or inhibits the HMTMF81 polypeptide by detecting the presence or absense of a signal generated from the interaction of the compound with the HMTMF81 polypeptide.

In a further preferred embodiment, the ligand is labeled or unlabeled LTD4 or LTC4. In further embodiment, the cell expressing HMTMF81 is obtained by transfecting a cell with expression system capable of producing HMTMF81 polypeptide.

In another embodiment, the method for identifying agonist or antagonist comprises the steps of:

(a) determining the inhibition of binding of a ligand to cells which have the HMTMF81 polypeptide (preferably that of SEQ ID NO: 2) on the surface thereof, or to cell membranes containing the polypeptide, in the presence of a candidate compound under conditions to permit binding to the polypeptide; and (b) determining the amount of ligand bound to the polypeptide, such that a compound capable of causing reduction of binding of a ligand is an agonist or antagonist.

Preferably, the ligand is labeled or unlabeled LTD4 or LTC4. In further embodiment, the cell which have HMTMF81 polypeptide, or cell membranes containing the polypeptide, is obtained by transfecting a cell with expression system capable of producing HMTMF81 polypeptide.

More specifically, a HMTMF81 polypeptide (receptor of the present invention) (preferably that of SEQ ID NO: 2) may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands, for example, cells, cell-free preparations, chemical libraries, and natural product mixtures. These substrates and ligands may be natural substrates and ligands or may be structural or functional mimetics. See Coligan, et al., Current Protocols in Immunology 1(2) :Chapter 5 (1991).

In general, such screening procedures involve providing appropriate cells which express a receptor polypeptide of the present invention on the surface thereof. Such cells include cells from mammals, yeast, Drosophila or *E. coli*. In particular, a polynucleotide encoding the receptor of the present invention is employed to transfect cells to thereby express a HMTMF81 polypeptide. The expressed receptor is then contacted with a test compound to observe binding, stimulation or inhibition of a functional response.

One such screening procedure involves the use of mammalian cells which are transfected to express a receptor of the present invention. The cells are loaded with an indicator dye that produces a fluorescent signal when bound to calcium, and the cells are contacted with a test substance and a receptor agonist, such as LTD4 or LTC4. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist (or agonist) for the receptor.

Another screening procedure involves the use of melanophores which are transfected to express a HMTMF81 polypeptide (preferably that of SEQ ID NO: 2). Such a screening technique is described in PCT WO 92/01810, published Feb. 6, 1992. Such an assay may be employed to screen for a compound which inhibits activation of a receptor of the present invention by contacting the melanophore cells which encode the receptor with both a receptor ligand, such as LTD4 or LTC4, and a compound to be screened. Inhibition of the signal generated by the ligand indicates that a compound is a potential antagonist for the receptor, i.e., inhibits activation of the receptor.

The technique may also be employed for screening of compounds which activate a receptor of the present invention by contacting such cells with compounds to be screened and determining whether such compound generates a signal, i.e., activates the receptor.

Other screening techniques include the use of cells which express a HMTMF81 polypeptide (for example, transfected CHO, COS or HEK 293 cells) (preferably that of SEQ ID NO: 2) in a system which measures extracellular pH changes caused by receptor activation. In this technique, compounds may be contacted with cells expressing a receptor polypeptide of the present invention. A second messenger response, e.g., signal transduction or pH changes, is then measured to determine whether the potential compound activates or inhibits the receptor.

Another screening technique involves expressing a HMTMF81 polypeptide (preferably that of SEQ ID NO: 2) in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists, and thus inhibit activation of a receptor polypeptide of the present invention by determining inhibition of binding of labeled ligand, such as LTD4 or LTC4, to cells which have the receptor on the surface thereof, or cell membranes containing the receptor. Such a method involves transfecting a eukaryotic cell, such as COS, CHO or HEK 293, with DNA encoding a HMTMF81 polypeptide such that the cell expresses the receptor on its surface. The cell is then contacted with a potential antagonist in the presence of a labeled form of a ligand, such as LTD4 or LTC4. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called a binding assay.

Another screening procedure involves use of mammalian cells which are transfected to express a receptor of the present invention, and which are also transfected with a reporter gene construct that is coupled to activation of the receptor (for example, luciferase or beta-galactosidase behind an appropriate promoter). The cells are contacted with a test substance and a receptor agonist, such LTD4 or LTC4, and the signal produced by the reporter gene is measured after a defined period of time. The signal can be measured using a luminometer, spectrophotometer, fluorimeter, or other such instrument appropriate for the specific reporter construct used. Inhibition of the signal generated by the ligand indicates that a compound is a potential antagonist for the receptor.

Another screening technique for antagonists or agonists involves introducing RNA encoding a HMTMF81 polypeptide into Xenopus oocytes to transiently or stably express the receptor. The receptor oocytes are then contacted with a receptor ligand, such as LTD4 or LTC4, and a compound to be screened. Inhibition or activation of the receptor is then determined by detection of a signal, such as, cAMP, calcium, proton, or other ions.

Another method involves screening for a HMTMF81 polypeptide inhibitors by determining inhibition or stimulation of HMTMF81 polypeptide-mediated cAMP and/or adenylate cyclase accumulation or diminution. Such a method involves transiently or stably transfecting a eukaryotic cell with a HMTMF81 polypeptide to express the receptor on the cell surface. The cell is then exposed to potential antagonists in the presence of HMTMF81 polypeptide ligand, such as LTD4 or LTC4. The amount of cAMP accumulation is then measured, for example, by radioimmunoassays or protein binding assays (for example using Flashplates or a scintillation proximity assay). Changes in cAMP levels can also be determined by directly measuring the activity of the enzyme, adenylyl cyclase, in broken cell preparations. If the potential antagonist binds the receptor, and thus inhibits HMTMF81 polypeptide binding, the levels of HMTMF81 polypeptide-mediated cAMP, or adenylate cyclase activity, will be reduced or increased.

Another screening method for agonists and antagonists relies on the endogenous pheromone response pathway in the yeast, *Saccharomyces cerevisiae*. Heterothallic strains of yeast can exist in two mitotically stable haploid mating types, MATa and MATα. Each cell type secretes a small peptide hormone that binds to a G-protein coupled receptor on opposite mating-type cells which triggers a MAP kinase cascade leading to G1 arrest as a prelude to cell fusion. Genetic alteration of certain genes in the pheromone response pathway can alter the normal response to pheromone, and heterologous expression and coupling of human G-protein coupled receptors and humanized G-protein subunits in yeast cells devoid of endogenous pheromone receptors can be linked to downstream signaling pathways and reporter genes (e.g., U.S. Pat. Nos. 5,063,154; 5,482,835; 5,691,188). Such genetic alterations include, but are not limited to, (i) deletion of the STE2 or STE3 gene encoding the endogenous G-protein coupled pheromone receptors; (ii) deletion of the FAR1 gene encoding a protein that normally associates with cyclin-dependent kinases leading to cell cycle arrest; and (iii) construction of reporter genes fused to the FUS1 gene promoter (where FUS1 encodes a membrane-anchored glycoprotein required for cell fusion). Downstream reporter genes can permit either a positive growth selection (e.g., histidine prototrophy using the FUS1-HIS3 reporter), or a colorimetric, fluorimetric or spectrophotometric readout, depending on the specific reporter construct used (e.g., b-galactosidase induction using a FUS1-LacZ reporter).

The yeast cells can be further engineered to express and secrete small peptides from random peptide libraries, some of which can permit autocrine activation of heterologously expressed human (or mammalian) G-protein coupled receptors (Broach, J. R. and Thorner, J. *Nature* 384: 14–16, 1996; Manfredi, et al., *Mol. Cell. Biol.* 16: 4700–4709, 1996). This provides a rapid direct growth selection (e.g, using the FUS1-HIS3 reporter) for surrogate peptide agonists that activate characterized or orphan receptors. Alternatively, yeast cells that functionally express human (or mammalian) G-protein coupled receptors linked to a reporter gene readout (e.g., FUS1-LacZ) can be used as a platform for high-throughput screening of known ligands, fractions of biological extracts and libraries of chemical compounds for either natural or surrogate ligands. Functional agonists of sufficient potency (whether natural or surrogate) can be used as screening tools in yeast cell-based assays for identifying G-protein coupled receptor antagonists. For this purpose, the yeast system offers advantages over mammalian expression systems due to its ease of utility and null receptor background (lack of endogenous G-protein coupled receptors) which often interferes with the ability to identify agonists or antagonists.

The present invention also provides a method for determining whether a ligand not known to be capable of binding to a HMTMF81 polypeptide can bind to such receptor which comprises contacting a mammalian cell which expresses a HMTMF81 polypeptide with the ligand, such as LTD4 or LTC4, under conditions permitting binding of candidate ligands to a HMTMF81 polypeptide, and detecting the presence of a candidate ligand which binds to the receptor thereby determining whether the ligand binds to the HMTMF81 polypeptide. The systems hereinabove described for determining agonists and/or antagonists may also be employed for determining ligands which bind to the receptor.

Examples of potential HMTMF81 polypeptide antagonists include antibodies or, in some cases, oligonucleotides, which bind to the receptor but do not elicit a second messenger response such that the activity of the receptor is prevented. Potential antagonists also include compounds which are closely related to a ligand of the HMTMF81 polypeptide, i.e., an analog of the ligand, which have lost biological function and when binding to the HMTMF81 polypeptide, elicit no response.

Another potential antagonist is a small molecule that binds to a HMTMF81 polypeptide, making the HMTMF81 polypeptide (receptor) inaccessible to ligands such that normal biological activity is prevented. Examples of small molecules include, but are not limited to, small peptides or peptide-like molecules.

Potential antagonists also include soluble forms of a HMTMF81 polypeptide, e.g., fragments of the polypeptide, which bind to the ligand and prevent the ligand from interacting with membrane bound HMTMF81 polypeptides. Potential antagonists also include antibodies that bind to the LTD4 or LTC4 and prevent the ligand from binding or activating the HMTMF81 receptor.

Thus in another aspect, the present invention relates to a screening kit for identifying agonists, antagonists, and/or ligands for HMTMF81 polypeptides, LTD4 and LTC4, and agonists and antagonists for interactions of HMTTMF81 polypeptide with LTD4 or LTC4, which comprises:

(a) HMTMF81 polypeptide, preferably that of SEQ ID NO: 2, and preferably further comprises labeled or unlabeled LTD4 or LTC4;

(b) a recombinant cell expressing a HMTMF81 polypeptide, preferably that of SEQ ID NO:2, and preferably further comprises labeled or unlabeled LTD4 or LTC4; or (c) a cell membrane expressing HMTMF81 polypeptide, preferably that of SEQ ID NO: 2, and preferably further comprises labeled or unlabeled LTD4 or LTC4.

It will be appreciated that in any such kit, (a), (b), or (c) may comprise a substantial component.

Prophylactic and Therapeutic Methods

This invention provides methods of treating an abnormal conditions related to both an excess of and insufficient amounts of HMTMF81 activity.

If the activity of HMTMF81 is in excess, several approaches are available. One approach comprises administering to a subject an inhibitor compound (antagonist) as hereinabove described along with a pharmaceutically acceptable carrier in an amount effective to inhibit activation by blocking binding of ligands to the HMTMF81, or by inhibiting a second signal, and thereby alleviating the abnormal condition.

In another approach, soluble forms of HMTMF81 polypeptides still capable of binding the ligand in competition with endogenous HMTMF81 may be administered. Typical embodiments of such competitors comprise fragments of the HMTMF81 polypeptide.

In still another approach, expression of the gene encoding endogenous HMTMF81 can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an under-expression of HMTMF81 and its activity, several approaches are also available. One approach comprises administering to a subject a therapeutically effective amount of a compound which activates HMTMF81, i.e., an agonist as described above, in combination with a pharmaceutically acceptable carrier, to thereby alleviate the abnormal condition. Alternatively, gene therapy may be employed to effect the endogenous production of HMTMF81 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996).

Formulation and Administration

Peptides (polypeptides), such as the soluble form of HMTMF81 polypeptides, and agonists and antagonist compounds, may be formulated in combination with a suitable pharmaceutical carrier. Such formulations comprise a therapeutically effective amount of the peptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Peptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

A search of a random cDNA sequence database from Human Genome Sciences consisting of short sequences known as expressed sequence tags (EST) with 7-TM domains encoding cDNA sequences using BLAST algorithm disclosed an EST which was homologous to a platelet activating factor (PAF) like 7-transmembrane receptor. Further analysis of the sequencing data indicated the presence of upstream stop codon followed by Met and the transmembrane domains 1, 2, 3 and 4. The clone was missing 3' DNA sequence (TMs 5, 6, 7, carboxy end and the stop codon). In order to obtain complete 3' end sequence, a 3' RACE PCR (Life Technologies) was performed using gene specific primers and human leukocyte plasmid library. PCR band was subcloned into PCR2.1 vector (Invitrogen) and sequenced. Assembly of the DNA sequence and further analysis indicated a full length clone. A map analysis of the DNA sequence using the GCG software indicated an open reading frame (ORF) consisting of 337 amino acid residues. Further analysis of the DNA sequence by FASTA and BLAST algorithms displayed the homology of this polypeptide sequence to the 7- transmembrane like G-protein coupled receptors. In addition, the hydrophobicity plot analysis using the lasergene protean software showed several features in common with G-protein linked receptors. Most prominent was the existence of seven hydrophobic regions of approximately 20–30 amino acids each, which are likely to represent membrane spanning domains providing the 7-transmembrane structural topology found among the G-protein linked superfamily of receptors. In order to confirm the identity of the clone further, gene specific PCR primers were designed using the nucleotide sequence of the open reading frame (ORF) and the DNA sequence was amplified from two libraries (human leukocyte and human spleen). Correct size PCR bands were subcloned into PCR2.1 vector from Invitrogen (San Diego, Calif.) and sequenced.

Example 2

Mammalian Cell Expression

The receptors of the present invention are expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN or pCDNA3 vector. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectable in about 50% of the G418-resistant clones analyzed.

Example 3

Ligand Bank for Binding and Functional Assays

A bank of over 200 putative receptor ligands has been assembled for screening. The bank comprises: transmitters, hormones and chemokines known to act via a human seven transmembrane (7TM) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e. calcium, cAMP, microphysiometer, oocyte electrophysiology, etc, see below) as well as binding assays.

Example 4

Ligand Binding Assays

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

Example 5

Functional Assay in Xenopus Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/mi. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure.. Recordings are made in $Ca^{2+}$ free Barth's medium at room temperature. The Xenopus system can be used to screen known ligands and tissue/cell extracts for activating ligands.

Example 6

Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

Example 7

Extract/Cell Supernatant Screening

A large number of mammalian receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequencially subfractionated until an activating ligand is isolated identified.

Example 8

Calcium and cAMP Functional Assays

7TM receptors which are expressed in HEK 293 cells have been shown to be coupled functionally to activation of PLC and calcium mobilization and/or cAMP stimuation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day>150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP flucuation are tested in vector control cells to determine if the response is unique to the transfected cells expressing receptor.

What is claimed is:

1. An isolated polynucleotide comprising a nucleotide sequence that has at least 95% identity to a nucleotide sequence encoding a polypeptide comprising the amino acid sequence of SEQ ID NO:2, said identity being over the entire region coding for SEQ ID NO:2 and calculated by $n_n \leq x_n - (x_n \cdot y)$, wherein $n_n$ is the number of nucleotide alterations in said isolated polynucleotide, $x_n$ is the total number of nucleotides encoding the amino acid sequence of SEQ ID NO:2, and y is 0.95.

2. The polynucleotide of claim 1 wherein said polynucleotide is DNA or RNA.

3. An isolated polynucleotide comprising a nucleotide sequence encoding a polypeptide comprising the amino acid of SEQ ID NO:2.

4. The isolated polynucleotide of claim 3 comprising the nucleotide sequence of SEQ ID NO:1.

5. The isolated polynucleotide of claim 3 consisting of the nucleotide sequence of SEQ ID NO: 1.

6. An expression vector comprising a polynucleotide encoding a polypeptide comprising the amino acid sequence of SEQ ID NO:2 when said expression vector is present in a compatible host cell.

7. A recombinant host cell comprising the expression vector of claim 6.

8. A process for producing a polypeptide comprising the amino acid sequence of SEQ ID NO:2, said process comprising culturing the recombinant host cell of claim 7 under conditions sufficient for the production of said polypeptide and recovering said polypeptide from the culture.

9. A process for producing a cell which produces a polypeptide comprising the amino acid sequence of SEQ ID NO:2, said process comprising transforming or transfecting a host cell with the expression vector of claim 6 such that the host cell, under appropriate culture conditions, produces said polypeptide.

10. An isolated polynucleotide which is complementary to a nucleotide sequence encoding a polypeptide comprising the amino acid sequence of SEQ ID NO:2.

11. The isolated polynucleotide of claim 10 wherein said isolated polynucleotide is complementary to the nucleotide sequence of SEQ ID NO:1.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1578 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
CGGCCGCCAG TGTGATGGAT ATCTGCAGAA TTCGGCTTTA CGGCTGCGAG AAGACGACAG        60

AAGGGGGAGG AAGAAGAATC TGTATATCTG TATATATTGG CTAGCAAATG TGCCCTGCTC       120

TCTCCCCTCT TAAAAATAGC AGCAACCCAT CTTTGCAAAG AAGCTTGCCT ATAGAGCAGG       180

CACTCTGTGA ATGGACTGTG CTTTTACGAC CCTACAGGGT ATCAAGATAC TGTGCAGCTC       240

GCCAACAAGG ATTAATTGCA AGGACTGGTA GATCGAATTT ACTGAAGACT TGGAGCTTGC       300
```

```
TTCTGAGAAC AAACGCAAAA GGACAGTAAA CTGTGGACCT TGAAGTTAGC AGCGTGGGCT    360

TCCTCTAATA TTACACCGTA AAAGGCATTG ATCACCATAA GAAGGAACAT TTGTGAAGGT    420

ACTCCAGTGC CAGAAAGAGG CACAAAGCAG ACATTCGTAG AGAAACATGG ATGAAACAGG    480

AAATCTGACA GTATCTTCTG CCACATGCCA TGACACTATT GATGACTTCC GCAATCAAGT    540

GTATTCCACC TTGTACTCTA TGATCTCTGT TGTAGGCTTC TTTGGCAATG CTTTGTGCT    600

CTATGTCCTC ATAAAAACCT ATCACAAGAA GTCAGCCTTC CAAGTATACA TGATTAATTT    660

AGCAGTAGCA GATCTACTTT GTGTGTGCAC ACTGCCTCTC CGTGTGGTCT ATTATGTCCA    720

CAAAGGCATT TGGCTCTTTG GTGACTTCTT GTGCCGCCTC AGCACCTATG CTTTGTATGT    780

CAACCTCTAT TGTAGCATCT TCTTTATGAC AGCCATGAGC TTTTTCCGGT GCATTGCAAT    840

TGTTTTTCCA GTCCAGAACA TTAATTTGGT TACACAGAAA AAAGCCAGGT TTGTGTGTGT    900

AGGTATTTGG ATTTTTGTGA TTTTGACCAG TTCTCCATTT CTAATGGCCA AACCACAAAA    960

AGATGGGAAA AATAATACCA AGTGCTTTGA GCCCCACAA GACAATCAAA CTAAAAATCA   1020

TGTTTTGGTC TTGCATTATG TGTCATTGTT TGTTGGCTTT ATCATCCCTT TTGTTATTAT   1080

AATTGTCTGT TACACAATGA TCATTTTGAC CTTACTAAAA AAATCAATGA AAAAAAATCT   1140

GTCAAGTCAT AAAAAGGCTA TAGGAATGAT CATGGTCGTG ACCGCTGCCT TTTTAGTCAG   1200

TTTCATGCCA TATCATATTC AACGTACCAT TCACCTTCAT TTTTTACACA ATGAAACTAA   1260

ACCCTGTGAT TCTGTCCTTA GAATGCAGAA GTCCGTGGTC ATAACCTTGT CTCTGGCTGC   1320

ATCCAATTGT TGCTTTGACC CTCTCCTATA TTTCTTTTCT GGGGGTAACT TTAGGAAAAG   1380

GCTGTCTACA TTTAGAAAGC ATTCTTTGTC CAGCGTGACT TATGTACCCA GAAGAAGGC   1440

CTCTTTGCCA GAAAAGGAG AAGAAATATG TAAAGTATAG TTTAAACCAT TTCCAGTCCA   1500

AACCAATGAA AATAGTTTCC CAAATAAGTA TTTTGTCAAA TCATTTACAA AAAAAAAAAA   1560

AAAAAAAAAA AAAAAAA                                                  1578
```

(2) INFORMATION FOR SEQ ID NO:2:

(i) SEQUENCE CHARACTERISTICS:
        (A) LENGTH: 337 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Asp Glu Thr Gly Asn Leu Thr Val Ser Ser Ala Thr Cys His Asp
 1               5                  10                  15

Thr Ile Asp Asp Phe Arg Asn Gln Val Tyr Ser Thr Leu Tyr Ser Met
                20                  25                  30

Ile Ser Val Val Gly Phe Phe Gly Asn Gly Phe Val Leu Tyr Val Leu
            35                  40                  45

Ile Lys Thr Tyr His Lys Lys Ser Ala Phe Gln Val Tyr Met Ile Asn
        50                  55                  60

Leu Ala Val Ala Asp Leu Leu Cys Val Cys Thr Leu Pro Leu Arg Val
65                  70                  75                  80

Val Tyr Tyr Val His Lys Gly Ile Trp Leu Phe Gly Asp Phe Leu Cys
                85                  90                  95

Arg Leu Ser Thr Tyr Ala Leu Tyr Val Asn Leu Tyr Cys Ser Ile Phe
                100                 105                 110
```

```
Phe Met Thr Ala Met Ser Phe Phe Arg Cys Ile Ala Ile Val Phe Pro
        115                 120                 125
Val Gln Asn Ile Asn Leu Val Thr Gln Lys Lys Ala Arg Phe Val Cys
        130                 135                 140
Val Gly Ile Trp Ile Phe Val Ile Leu Thr Ser Ser Pro Phe Leu Met
145                     150                 155                 160
Ala Lys Pro Gln Lys Asp Gly Lys Asn Asn Thr Lys Cys Phe Glu Pro
                165                 170                 175
Pro Gln Asp Asn Gln Thr Lys Asn His Val Leu Val Leu His Tyr Val
            180                 185                 190
Ser Leu Phe Val Gly Phe Ile Ile Pro Phe Val Ile Ile Ile Val Cys
        195                 200                 205
Tyr Thr Met Ile Ile Leu Thr Leu Leu Lys Lys Ser Met Lys Lys Asn
        210                 215                 220
Leu Ser Ser His Lys Lys Ala Ile Gly Met Ile Met Val Val Thr Ala
225                 230                 235                 240
Ala Phe Leu Val Ser Phe Met Pro Tyr His Ile Gln Arg Thr Ile His
                245                 250                 255
Leu His Phe Leu His Asn Glu Thr Lys Pro Cys Asp Ser Val Leu Arg
            260                 265                 270
Met Gln Lys Ser Val Val Ile Thr Leu Ser Leu Ala Ala Ser Asn Cys
        275                 280                 285
Cys Phe Asp Pro Leu Leu Tyr Phe Phe Ser Gly Gly Asn Phe Arg Lys
        290                 295                 300
Arg Leu Ser Thr Phe Arg Lys His Ser Leu Ser Ser Val Thr Tyr Val
305                 310                 315                 320
Pro Arg Lys Lys Ala Ser Leu Pro Glu Lys Gly Glu Glu Ile Cys Lys
                325                 330                 335
Val
```